(12) United States Patent
Hallack et al.

(10) Patent No.: US 11,071,497 B2
(45) Date of Patent: Jul. 27, 2021

(54) WEARABLE MEDICAL DEVICE

(71) Applicant: GENTEX CORPORATION, Zeeland, MI (US)

(72) Inventors: Jason D. Hallack, Allendale, MI (US); Thomas S. Wright, Holland, MI (US); Joshua D. Lintz, Allendale, MI (US); Kurtis L. Geerlings, Zeeland, MI (US); Bradley R. Hamlin, Allendale, MI (US)

(73) Assignee: GENTEX CORPORATION, Zeeland, MI (US)

( * ) Notice: Subject to any disclaimer, the term of this patent is extended or adjusted under 35 U.S.C. 154(b) by 0 days.

(21) Appl. No.: 16/889,048

(22) Filed: Jun. 1, 2020

(65) Prior Publication Data
US 2020/0390392 A1 Dec. 17, 2020

Related U.S. Application Data

(60) Provisional application No. 62/860,008, filed on Jun. 11, 2019.

(51) Int. Cl.
| | |
|---|---|
| *A61B 5/00* | (2006.01) |
| *A61B 5/1171* | (2016.01) |
| *A61B 90/30* | (2016.01) |
| *G02C 7/12* | (2006.01) |
| *G02C 11/04* | (2006.01) |
| *G02C 7/08* | (2006.01) |
| *F21V 33/00* | (2006.01) |

(Continued)

(52) U.S. Cl.
CPC .......... *A61B 5/6803* (2013.01); *A61B 5/1176* (2013.01); *A61B 90/30* (2016.02); *G02C 7/088* (2013.01); *G02C 7/12* (2013.01); *G02C 11/04* (2013.01); *A61B 2505/05* (2013.01); *F21V 33/0068* (2013.01); *F21W 2131/20* (2013.01); *F21W 2131/205* (2013.01)

(58) Field of Classification Search
CPC ............ F21V 23/0464; F21V 33/0068; F21W 2131/20; F21W 2131/205; G02C 11/04; A61B 2090/309; A61B 2505/05; A61B 5/1176; A61B 5/6803; A61B 90/30
See application file for complete search history.

(56) References Cited

U.S. PATENT DOCUMENTS

| | | | | |
|---|---|---|---|---|
| RE46,463 E | * | 7/2017 | Fienbloom | ............... F21L 14/00 |
| 9,717,401 B1 | * | 8/2017 | Orringer | ................... F21V 5/04 |

(Continued)

FOREIGN PATENT DOCUMENTS

WO     2018002674 A1     1/2018

OTHER PUBLICATIONS

International Search Report dated Aug. 27, 2020, for correspondence PCT application No. PCT/US2020/025520, 2 pages.

(Continued)

*Primary Examiner* — Zheng Song
(74) *Attorney, Agent, or Firm* — Price Heneveld LLP; Bradley D. Johnson (57) ABSTRACT

A wearable medical device includes a frame and a lens coupled to the frame. The lens is configured to be positioned proximate eyes of a user. At least one lamp device is coupled to the frame. The at least one lamp device emits light forward from the frame. A controller activates and controls the at least one lamp device.

17 Claims, 5 Drawing Sheets

(51) Int. Cl.
*F21W 131/20* (2006.01)
*F21W 131/205* (2006.01)

(56) References Cited

U.S. PATENT DOCUMENTS

| | | | |
|---|---|---|---|
| 9,807,291 B1* | 10/2017 | Tome | G11B 27/031 |
| 10,039,445 B1* | 8/2018 | Torch | A61B 5/165 |
| 10,071,180 B1 | 9/2018 | Miao et al. | |
| 10,935,815 B1 | 3/2021 | Castañeda | |
| 10,935,816 B2 | 3/2021 | Ban | |
| 2001/0021108 A1* | 9/2001 | Shimada | G02C 11/04 |
| | | | 362/103 |
| 2005/0099799 A1* | 5/2005 | Cugini | G02C 11/04 |
| | | | 362/105 |
| 2012/0120635 A1* | 5/2012 | Strong | F21V 5/008 |
| | | | 362/105 |
| 2015/0018622 A1 | 1/2015 | Tesar et al. | |
| 2017/0307880 A1* | 10/2017 | Shrubsole | G02B 27/017 |
| 2018/0224674 A1* | 8/2018 | Carabin | A61C 5/00 |
| 2019/0060026 A1* | 2/2019 | Geerlings | A61B 90/39 |
| 2019/0254143 A1* | 8/2019 | Hallack | H04N 5/2354 |

OTHER PUBLICATIONS

Written Opinion dated Aug. 27, 2020, for correspondence PCT application No. PCT/US2020/025520, 5 pages.

* cited by examiner

WEARABLE MEDICAL DEVICE

CROSS REFERENCE TO RELATED APPLICATIONS

This application claims the benefit of and priority to U.S. Provisional Patent Application No. 62/860,008, filed on Jun. 11, 2019, entitled "Wearable Medical Device," the entire disclosure of which is hereby incorporated herein by reference.

FIELD OF THE DISCLOSURE

The present disclosure generally relates to a medical device, and more particularly to a wearable medical device for a surgical suite.

SUMMARY OF THE DISCLOSURE

According to an aspect, a wearable medical device may comprise a frame; a support mechanism secured to the frame and configured to hold the frame in place on a user's head; at least one sensor; an imager supported by the frame; and a controller in communication with the at least one sensor and the imager. The imager may be configured to capture and record images and to detect intensity of lighting in the environment surrounding the imager and to send a signal corresponding to the lighting intensity to the controller. The wearable medical device further may comprise at least one imager having an imager lens, the imager supported by the frame and in communication with the controller. The at least one imager may be configured to capture and record images. The imager lens may be polarized. The controller may be configured to process the captured images for stabilization data relating to one of the image and the lighting in the image. The wearable medical device further may comprise at least one lamp device having a light source, the at least one lamp device removably securable to the frame and configured to be in communication with the controller. The imager may be configured to detect intensity of lighting in the environment surrounding the imager to send a corresponding signal to the controller. The controller may be configured to, upon receipt of the corresponding signal from the imager, adjust the intensity of light emitted from the lamp device in response to the signal.

The imager may include facial recognition functions. Upon capturing an image with a person's face, the imager may be configured to send a signal to the controller; and, upon receipt of the signal, the controller may be configured to deactivate the lamp device. The imager may be configured to detect display screens. Upon detecting a display screen, the imager may be configured to send a signal to the controller; and, upon receipt of the signal from the imager, the controller may be configured to deactivate the lamp device. The wearable medical device further may comprise at least one lens coupled to the frame and configured to be positioned proximate eyes of a user when the wearable medical device may be worn on a user's head. The wearable medical device further may comprise at least one image sensor disposed on the lens. The at least one image sensor may be configured to capture eye image data of the user. The at least one image sensor may be configured to transmit inputs to the controller. The controller may be configured to, based on inputs received from the at least one image sensor, direct light emitted from the lamp device in a direction that substantially coincides with the direction of focus of the user. The at least one lamp device may comprise movable optics capable of redirecting light from the light source in response to a received input. The controller may be configured to: process image data from images captured by the imager; identify shadows and luminosity; and adjust an intensity of the at least one lamp device based on the shadows and luminosity. The wearable medical device further may include a microphone disposed on the frame and configured to record sounds proximate the wearable medical device and to send audio information to one of the controller and an audio storage.

According to another aspect, a surgical suite illumination system may comprise a light assembly, comprising one or more light sources having adjustable intensity; and one or more positioning devices operable to move the light assembly between a plurality of positions; and a wearable medical device, comprising a frame, a support member secured to the frame and configured to hold the frame in place on a user's head; at least one sensor; and a controller in communication with the at least one sensor and with the light assembly. The controller may be configured to cause the light assembly to move based on inputs received from the at least one sensor. The controller may be capable of causing the one or more light sources of the light assembly to change the intensity of the light they emit. The wearable medical device further may comprise an infrared sensor in communication with the controller and configured to detect infrared patterns. The light assembly may be configured to emit infrared patterns; and the controller may be configured to use the detected infrared patterns from the wearable medical device to determine a relative position of the light assembly. The at least one sensor may be configured to determine where a user may be looking; and wherein the controller may be configured to position the light assembly to provide light where the user may be looking. The surgical suite illumination system may further comprising an imager in communication with the controller and configured to capture image data; wherein the controller is configured to: process image data from images captured by the imager; identify shadows and luminosity; and cause the one or more positioning devices to move the light assembly based on the shadows and luminosity.

According to another aspect of the present disclosure, a wearable medical device includes a frame and a lens coupled to the frame. The lens is configured to be positioned proximate to eyes of a user. At least one lamp device is coupled to the frame. The at least one lamp device emits light outward from the frame. A controller activates and controls the at least one lamp device.

According to another aspect of the present disclosure, a surgical suite illumination assembly includes a light assembly and a positioning device coupled to the light assembly. The light assembly is operable between a plurality of positions via the positioning device. A wearable medical device includes a frame, a lens coupled to the frame, and an image sensor coupled to the lens and configured to sense eye movement of a user. A controller controls at least one of the positioning device and the light assembly in response to the eye movement sensed by the image sensor.

These and other features, advantages, and objects of the present disclosure will be further understood and appreciated by those skilled in the art by reference to the following specification, claims, and appended drawings.

DETAILED DESCRIPTION

Referring to FIGS. 1-5, reference numeral 10 generally designates a wearable medical device including a frame 14. A lens 18 may be coupled to the frame 14. The lens 18 may be configured to be positioned proximate eyes 22 of a user 26. A lamp device 30 may be coupled to the frame 14. The lamp device 30 may be configured to emit light 34 outward from the frame 14. A controller 38 activates and controls the lamp device 30.

Figure 1:
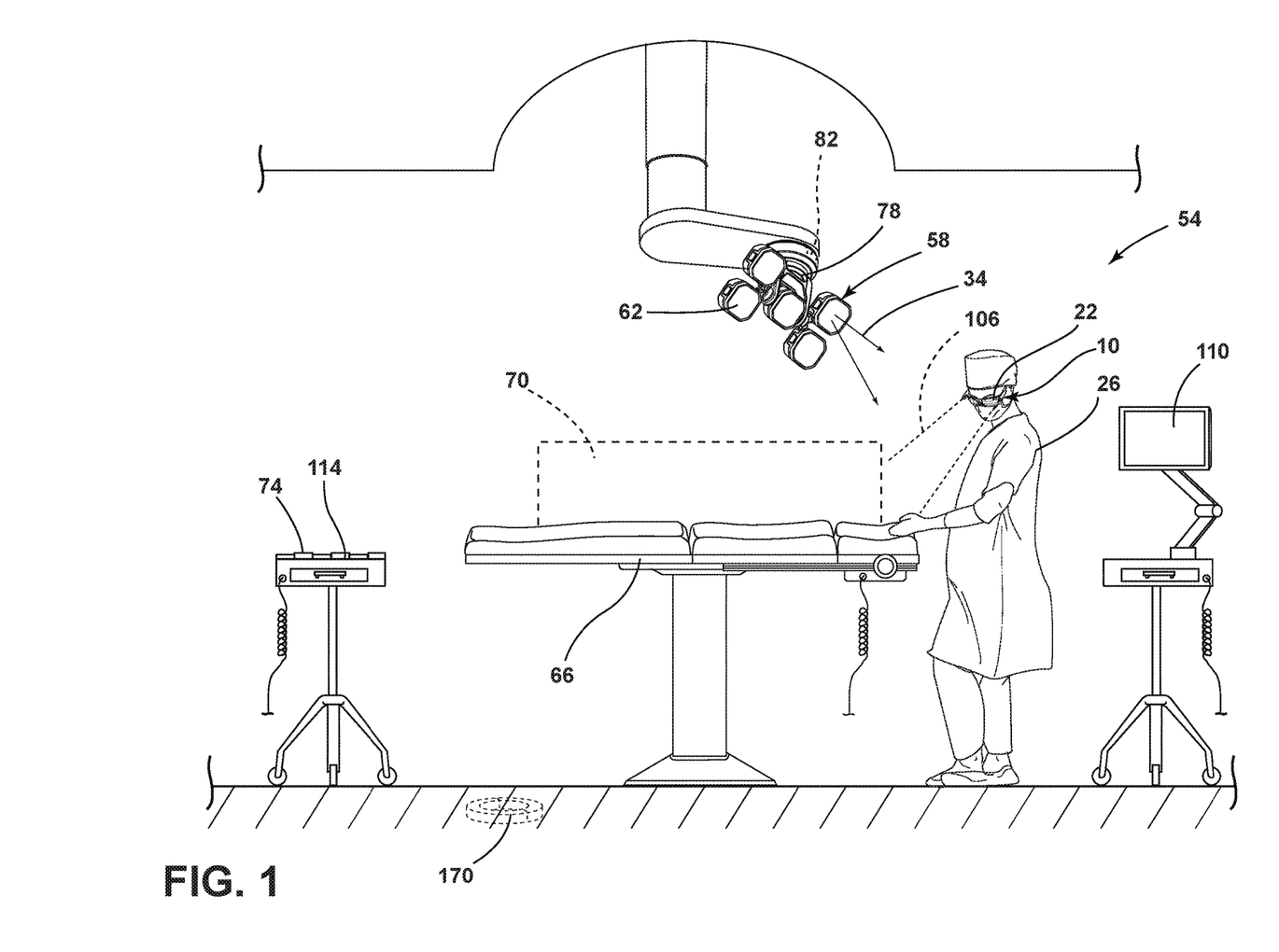
FIG. 1 is a schematic view of a surgical suite with a wearable medical device, according to one example.

Referring to FIG. 1, the user 26 (e.g., a surgeon, doctor, or other healthcare provider) is illustrated wearing the wearable medical device 10 in a surgical suite 54. While illustrated with the surgeon in the surgical suite 54, the wearable medical device 10 may be used and/or worn by other medical professionals, other users 26 in a medical setting, and/or other environments. The surgical suite 54 may include a light assembly 58, including one or more light sources 62. Light assembly 58 may be disposed above a table 66. The table 66 may at least partially define a surgical field 70. For purposes of this disclosure, the surgical field 70 may be an operating field, which may be an isolated area where surgery is performed. Within the surgical suite 54, there may be one or more tools or instruments 74 that may be utilized in various procedures.

The light assembly 58 may include one or more positioning devices 78. The positioning devices 78 operate to move the light assembly 58 between a plurality of positions. The positioning devices 78 may translate the light assembly 58 to different areas of the surgical suite 54. Additionally, the positioning devices 78 may rotate and/or angle the light assembly 58 to direct light 34 emitted from the light sources 62 in a selected direction or at a selected area. The positioning devices 78 may be driven by a motor 82 that repositions the light assembly 58. The motor 82 may be, for example, a servo motor or a stepper motor. Further, the light assembly 58 may include more than one motor 82 for different movements of the positioning devices 78.

Figure 2:
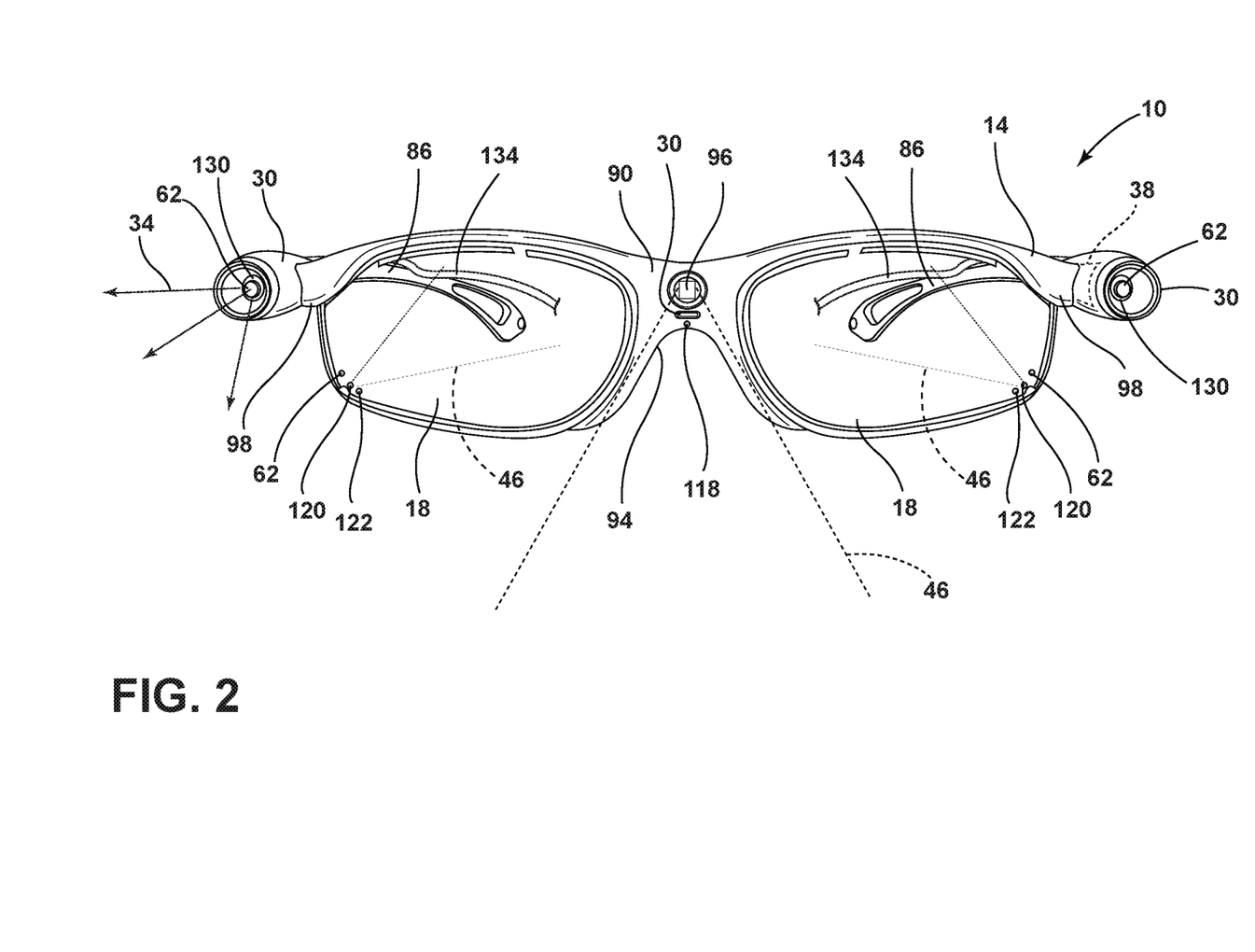
FIG. 2 is a front perspective view of a wearable medical device, according to one example.

Referring to FIGS. 1 and 2, as shown, the wearable medical device 10 may further comprise a support member secured to the wearable medical device and configured to allow the wearable medical device 10 to be temporarily secured to the head of a user. The support member may comprise, for example, arms 86 or a flexible strap or straps. In some embodiments, the frame 14 and the lens 18 of the wearable medical device 10 may be formed to resemble glasses or eyewear. Accordingly, the frame 14 may include two arms 86 to allow the user 26 to wear the wearable medical device 10 in a manner similar to glasses. Additionally or alternatively, at least one flexible strap may be secured to the sides of the frame and be configured to extend around a head of a user, thereby holding the frame in place on the user's head. A center portion 90 of the frame 14 may define an indent 94 for resting the frame 14 on a nose of the user 26. The wearable medical device 10, as illustrated in FIG. 2, includes two lenses 18 separated by the center portion 90 of the frame 14. Alternatively, the wearable medical device 10 may include a single lens 18 that extends between opposing side portions 98 of the frame 14. It is also contemplated that the wearable medical device 10 may be configured as a headlamp or other wearable device without departing from the teachings herein. In some embodiments, the wearable medical device 10 may comprise a face shield (not shown) secured to the frame in addition to or instead of a lens or lenses.

The wearable medical device 10 may include an imager 96 disposed on the center portion 90 of the frame 14. The imager 96 may be a camera or other vision-based device. The imager 96 may be an area-type imager, such as a charge-coupled device (CCD) or a complementary metal-oxide semiconductor (CMOS) imager. According to various examples, the imager 96 may include one or more lenses to collimate and/or focus the light reflected by a patient, the table 66, or other features of the surgical suite 54. Stated differently, the lenses of the imager 96 may be polarized to utilize the emitted light 34 from the light assembly 58 in the surgical suite 54. The imager 96 has a field of view 46 that extends outwardly from the frame 14. In various examples, the field of view 46 extends forward from the user 26 when the user 26 is wearing the wearable medical device 10.

Figure 5:
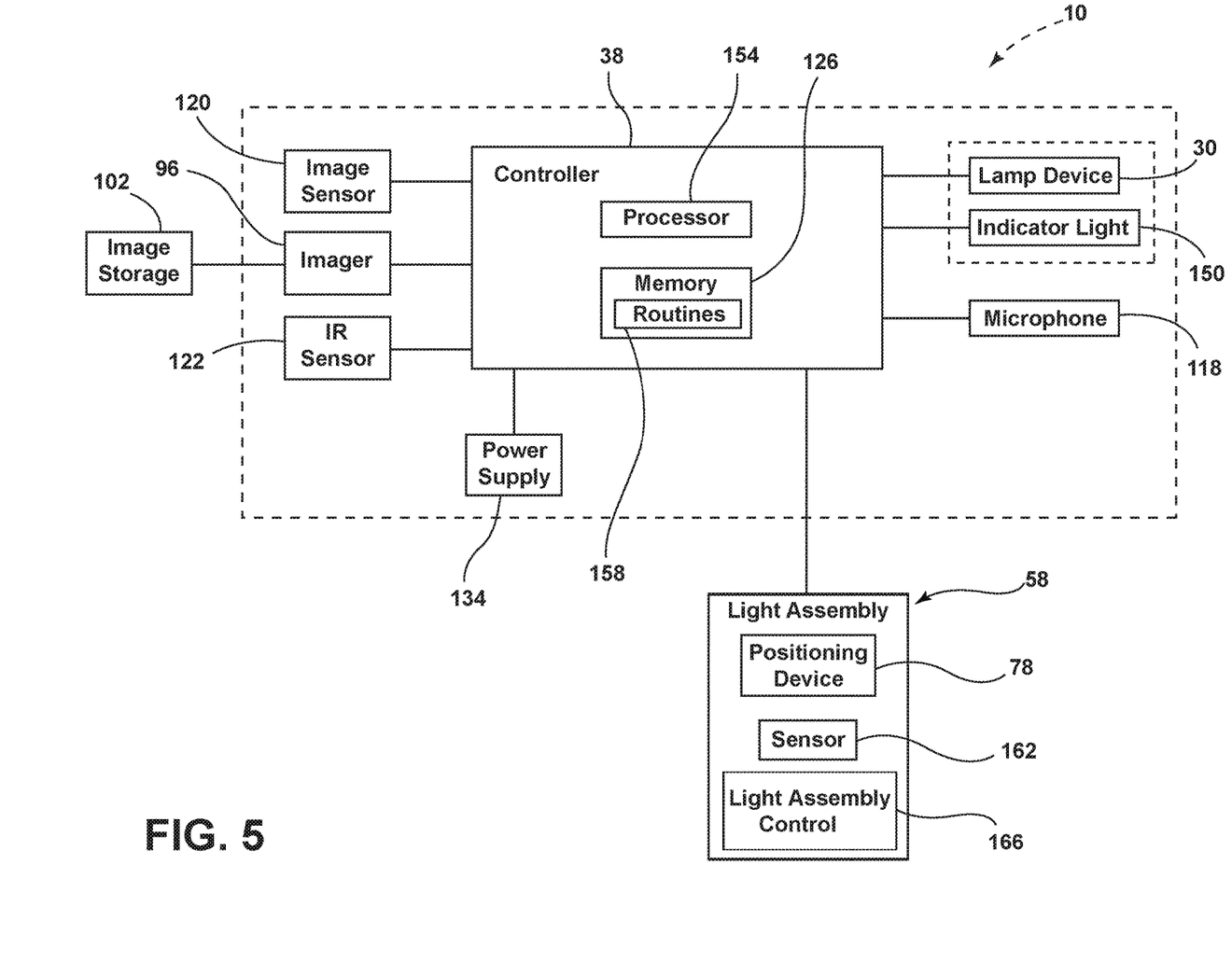
FIG. 5 is a block diagram of a surgical suite illumination assembly including a wearable medical device, according to one example.

Referring still to FIGS. 1 and 2, the imager 96 may be configured to capture and record images in the field of view 46 and the recorded images may be output to an image storage 102 (FIG. 5). The recorded images may be still images and/or videos. Recording the images within the field of view 46 may be advantageous for viewing the recordings at a later time for teaching other medical professionals and/or students. According to various aspects, the imager 96 is disposed substantially in line with the eyes 22 of the user 26, allowing the field of view 46 to substantially overlap with a field of vision 106 of the user 26. Accordingly, the captured images may reflect the tasks and events that occur within the field of vision 106 of the user 26, which may be advantageous for capturing images that reflect the surgeon's point of view in the environment within the surgical suite 54. The imager 96 may be operably coupled to the image storage 102 via one or more wireless protocols (e.g., Bluetooth®; Wi-Fi (802.11a, b, g, n, etc.); ZigBee®; and Z-Wave®; etc.).

The images captured by the imager 96 may be processed by a controller 38. It is contemplated that the controller 38 may be directly coupled to and/or integrated into the wearable medical device 10, or may be a separate controller 38 for processing the captured images. In various examples, the captured images are processed for stabilization data relating to the image itself and/or lighting in the image. The stabilization data refers to data reflecting the movement of the user 26 while wearing the wearable medical device 10. For example, the wearable medical device 10 moves when the user 26 moves his or her head, resulting in a change of the field of view 46 of the imager 96. In various aspects, the lamp device 30 emits the light 34 in a selected direction based on a user command. When the head of the user 26 moves while the user 26 is wearing the wearable medical device 10, the emitted light 34 may not be emitted in the selected direction or at a selected area based on the new head position relative to the patient. This change in the direction of the emitted light 34 is captured by the imager 96 and the controller 38 determines whether and/or how the direction of the emitted light 34 may be adjusted based on the new head position of the user 26.

According to various aspects, the imager 96 may also map intensity of lighting (e.g., brightness) within the field of view 46 and/or the surgical suite 54. Stated differently, the imager 96 may detect the intensity of the lighting in the surrounding environment (e.g., the surgical suite 54) and send a corresponding signal to the controller 38. The controller 38 may then adjust the intensity of the emitted light 34 from the lamp device 30 and/or the light assembly 58 in response to the signal from the imager 96. For example, if the imager 96 detects that the intensity of light 34 in the surgical suite 54 is below a predefined intensity as determined by the controller 38, the controller 38 may increase the intensity of the light emitted from the lamp device 30, the light assembly 58, and/or a combination thereof until the brightness of the surgical suite 54 reaches the predefined intensity level. Alternatively, if the light 34 intensity in the surgical suite 54 is above a predefined threshold, the controller 38 may lower the intensity of the light 34 emitted from the lamp device 30, the light assembly 58, and/or a combination thereof. Mapping the intensity of the lighting may be advantageous for providing a brightness level suitable for performing various surgical operations and other medical procedures within the surgical suite 54. In this way, if the lighting in the surgical suite 54 is too bright or too dim to provide suitable cavity lighting (e.g., lighting in the cavity formed by the surgical procedure), then the lighting may be adjusted accordingly.

Referring still to FIGS. 1 and 2, according to various aspects, the imager 96 may include facial recognition functions. The facial recognition functions may include one or more algorithms to detect or identify selected facial features to determine if the image captured by the imager 96 includes a person's face. Stated differently, the imager 96 may detect if the person's face is in the field of view 46 of the imager 96 and sends a corresponding signal to the controller 38. Alternatively, the captured images may be processed by the controller 38 to determine whether the person's face is within the image, and therefore within the field of view 46. The controller 38 may control the lamp device 30 in response to the person's face being detected in the field of view 46. Stated differently, if the imager 96 captures an image with the person's face, the imager 96 sends a signal to the controller 38, and the controller 38 may deactivate the lamp device 30 to prevent the lamp device 30 from emitting light 34 at the person's face.

Similarly, the imager 96 may also be configured to detect display screens 110. In this way, the imager 96 may detect light being emitted from the display screens 110. The controller 38 may deactivate the lamp device 30 when the imager 96 captures an image of a display screen 110. This may be advantageous so the user 26 of the wearable medical device 10 can view information on the display screen 110 without interference from the light 34 emitted from the lamp device 30.

Further, it is also contemplated that the imager 96 may be configured to track location and use of the instruments 74. For example, the instruments 74 may include a paint, indicator, and/or marker 114, which can be detected (e.g., infrared reflective and/or fluorescent) by the imager 96. Additionally or alternatively, the instruments 74 may be coded based on type (e.g., consumable tool versus non-consumable tool) and/or by the user operating them. According to various aspects, the instruments 74 may include a radio frequency identification tracking device, which may be identified by the controller 38 for presence detection and location-based triangulation or other methods. Accordingly, the instruments 74 may be tracked as they enter the field of view 46 of the imager 96.

In various aspects, the wearable medical device 10 includes a microphone 118 disposed on the frame 14 proximate the imager 96. The microphone 118 may be selectively activated and deactivated through a user command, a specified object detected within the field of view 46, or other factors. The microphone 118 may record sounds proximate the wearable medical device 10, and send audio information to the controller 38 and/or an audio storage. In this way, the audio data surrounding the surgical operation or other medical procedure may be recorded and viewed and/or listened to at a later time, which may be advantageous for teaching medical professionals and/or students.

Referring still to FIGS. 1 and 2, the wearable medical device 10 may include image sensors 120 disposed on the lens 18. According to various aspects, the image sensors 120 may be cameras or other vision-based devices. The image sensors 120 may be area-type image sensors 120, such as charge-coupled device (CCD) or complementary metal-oxide semiconductor (CMOS) sensors. According to various examples, the image sensors 120 may include one or more lenses to collimate and/or focus the light reflected by the patient, the table 66, or other features of the surgical suite 54. Stated differently, the lenses of the image sensors 120 may be polarized to utilize the emitted light 34 from the light assembly 58 in the surgical suite 54. The image sensors 120 may be the same area-type sensors as the imager 96, or may be different types of sensors to maximize efficiency and/or accuracy of different functions. As illustrated, the wearable medical device 10 includes one image sensor 120 proximate a left eye of the user 26 and one image sensor 120 proximate a right eye of the user 26 when the user 26 is wearing the wearable medical device 10. However, the wearable medical device 10 may include any number of image sensors 120 without departing from the teachings herein. The image sensors 120 each have the field of view 46 that extends outwardly from the frame 14. The image sensors 120 are configured to capture eye image data, such as, for example, eye movement of the user 26 within the fields of view 46. According to various aspects, the field of view 46 of the imager 96 extends forward and away from the user 26 when the user is wearing the wearable medical device 10, and the field of view 46 of the image sensors 120 extend in an opposing direction to that of the field of view 46 of the imager 96 towards the user 26 to capture the eye image data. The captured images may be transmitted to the controller 38 and/or to the image storage 102 (FIG. 5), similar to the imager 96.

Additionally or alternatively, the wearable medical device 10 may include infrared (IR) sensors 122 disposed on the lenses 18 proximate the image sensors 120. The wearable medical device 10 illustrated in FIG. 2 includes one IR sensor 122 proximate each of the left and right eyes 22 of the user 26. However, the number of IR sensors 122 may differ without departing from the teachings herein. The IR sensors 122 may work in conjunction with, and/or independently of, the image sensors 120. Further, the IR sensors 122 may also detect the eye movement of the user 26. In various examples, the wearable medical device 10 includes an iris authentication function, which may be at least partially performed by the IR sensors 122 and/or the image sensors 120. The iris authentication function may utilize IR illumination of an iris of the eye 22 of the user 26 in order to illuminate the eye 22 for identification of the user 26. Such illumination may be optimized in conditions allowing for high optical transmittance in the near-infrared (NIR) range. The image sensors 120 may be in communication with at least one light source 62 in the visible light spectrum, or may correspond to at least one infrared emitter configured to output an emission of light 34 in the NIR range (e.g., about 700 nm to about 940 nm). The image sensors 120 may be configured to selectively activate the infrared emitters corresponding to the light source 62 to illuminate the iris, such that an identity of a user 26 of the wearable medical device 10 may be determined. Stated differently, the eyes 22 of the user 26 may be illuminated such that the image sensors 120 may capture an image for iris authentication. Once the user 26 is determined, the controller 38 may authorize use of various components of the wearable medical device 10 based on predefined and/or stored personal settings for selected users 26.

Referring still to FIGS. 1 and 2, the image sensors 120 may be configured to track the eye movement of the user 26. In this way, the image sensors 120 may sense or detect the direction of focus of the user 26 (e.g., eye direction) relative to the head of the user 26. The direction of focus of the user 26 may be communicated to the controller 38, providing the controller 38 with information to direct the emitted light 34 from the lamp device 30 in a direction that substantially coincides with the direction of focus of the user 26. The direction of focus of the user 26 may also be determined by measuring an eye-ellipse. The eye-ellipse is a graphical device that represents the approximation of the eye location distribution of the user 26 as a multidimensional normal density distribution. The eye-ellipse results in a set of lines that isolate the ellipse area, which may account for about 90% of eye positions. Accordingly, the eye-ellipse may be utilized to track the eye position of the user 26.

In various examples, the image sensors 120 distinguish basic commands based on detected eye movement. Various eye movements may correspond with an instruction or command signal sent to the controller 38, such that a corresponding function may be performed. Additionally, the controller 38 may include one or more algorithms for processing the images to identify the user commands. For example, a specified eye movement (e.g., look left, look right, etc.) for a designated amount of time may be indicative of a command. The instruction signal may relate to the positioning and/or intensity of the emitted light 34 from the lamp device 30 and/or light assembly 58. Additionally or alternatively, the eye movements may correspond with instructions for different functions of the imager 96, the image sensors 120, the microphone 118, or other aspects of the wearable medical device 10.

With further reference to FIG. 2, the image sensors 120 may also sense a pupil size of the user 26. The information relating to pupil size may be communicated to the controller 38. The controller 38 may determine whether the pupil size is larger or smaller than baseline parameters of the pupil size of the user 26. The baseline may be determined when the user 26 initially activates the image sensors 120. Alternatively, the baseline pupil size may be stored in a memory 126 (FIG. 5) of the controller 38 and may be identified and recalled after the iris authentication of the user 26. The pupil size may indicate whether the lighting in the surgical suite 54 is too bright or too dim, and the controller 38 may adjust the emitted light 34 of the lamp device 30 and/or the light assembly 58 in response.

Further, the image sensors 120 may capture images of the eyes 22 of the user 26 and the controller 38 may include one or more algorithms for processing the images for fatigue metrics. Fatigue metrics may include comparing the captured eye image data with baseline information. For example, the baseline information can include an average percent that the eyes 22 of the user 26 are opened. The image sensors 120 may periodically sense the opening of the eyes 22 and the controller 38 may compare the sensed information with the baseline information. The controller 38 may also determine trends of a decreasing percent of eye-opening over a period or range of time. Additionally or alternatively, the image sensors 120 may sense when the user 26 blinks and send a corresponding signal to the controller 38. The controller 38 may determine if the number of times the user 26 blinks has increased or decreased over a period of time. According to various aspects, pupil location sensed by the image sensors 120 may also be a fatigue metric. The controller 38 may determine whether the user 26 is consciously focusing and/or thinking based on the sensed pupil location over a period of time.

Each of the imager 96, the microphone 118, the image sensors 120, the light sources 62 of the lamp devices 30, and the IR sensors 122 may be disposed on one or more circuits 130, such as a printed circuit board, in communication with the controller 38. The one or more circuit 130 may be rigid or flexible circuits. Further, each of the imager 96, the microphone 118, the image sensors 120, the light sources 62 of the lamp devices 30, and the IR sensors 122 may be disposed on a separate circuit 130, or several of these components may be disposed on a single circuit 130. Moreover, the wearable medical device 10 may include a power supply 134. The power supply 134 may be integrated with or, alternatively, external to the wearable medical device 10. The power supply 134 may also be rechargeable and may be configured to be charged during use.

Figure 3:
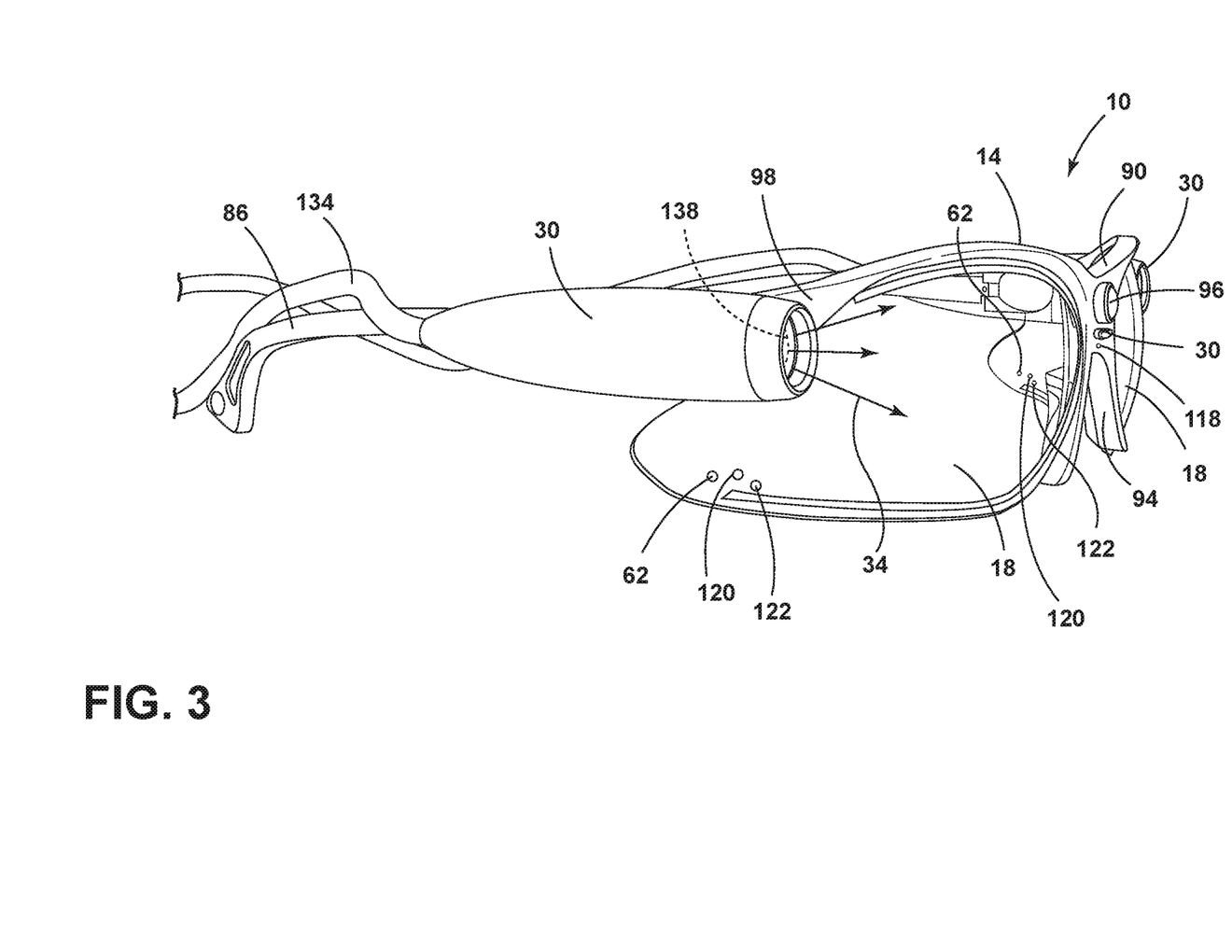
FIG. 3 is a side perspective view of the wearable medical device of FIG. 2.

Referring now to FIGS. 2 and 3, the wearable medical device 10 may include one or more lamp devices 30 without departing from the teachings herein. For example, the wearable medical device 10 is illustrated having two lamp devices 30. The two lamp devices 30 may be coupled to the opposing side portions 98 of the frame 14. Additionally or alternatively, the wearable medical device 10 may include a lamp device 30 disposed on the center portion 90 of the frame 14 proximate the imager 96. In examples with at least one lamp device 30 coupled to each of the opposing side portions 98 of the frame 14, the light 34 emitted from the lamp devices 30 may be angled toward the opposing lamp device 30 to reduce shadowing in the surgical field 70. If a single emission of light 34 is directed at a specified area at an angle, the light 34 may cause shadows. However, emission of the angled light 34 from more than one lamp device 30 may be advantageous for reducing and/or minimizing the shadowing in the surgical field 70.

According to various aspects, the lamp devices 30 include movable optics 138. The movable optics 138 may be movable via one or more motors 82 or any other similar devices known in the art. Further, the movable optics 138 may be moved in response to a command given by the user 26 via the eye movement as detected by the image sensors 120 and/or the controller 38. The movable optics 138 may redirect the emitted light 34 toward a selected area. Additionally or alternatively, the redirection of the light 34 may occur in response to the stabilization data processed by the controller 38, as previously discussed herein. When the user 26 moves their head, the movable optics 138 may redirect the emitted light 34 of at least one of the lamp devices 30. The redirected light 34 may be moved to the selected area based on the movement of the head and/or the detected eye movement of the user 26. The movable optics 138 may also adjust the size of a light spot 142 (FIG. 4) produced by the emitted light 34. The size of the light spot 142 may be increased or decreased in response to a detected condition within the surgical suite 54, the cavity lighting, and/or a user command.

According to various aspects, the lamp devices 30 may be activated when the image sensors 120, and/or the imager 96, detect inadequate cavity lighting, as determined by the controller 38. Accordingly, the controller 38, the imager 96, and/or the image sensors 120 may include one or more algorithms for detecting the cavity lighting and comparing the cavity lighting to a predefined level of cavity lighting. Additionally or alternatively, the predefined level of cavity lighting may be based on pupil size of the user 26, detected shadows in the cavity, and/or other aspects. Moreover, if there is adequate lighting in the cavity, the lamp devices 30 may remain deactivated or in a current setting. Additionally or alternatively, if the cavity lighting becomes too bright, the lamp devices 30 may be deactivated or the intensity of the emitted light 34 may be reduced. As previously explained, the imager 96 may capture images and the controller 38 may detect if the person's face and/or the display screen 110 is within the captured images. This information also affects the activation and deactivation of the lamp devices 30. When at least one of a person's face or a display screen 110 is detected within the captured images of the imager 96, the lamp devices 30 may be deactivated. The selective activation of the lamp devices 30 may reduce weight, size, and/or heat carried on the head of the user 26 with the wearable medical device 10.

Referring still to FIGS. 2 and 3, the lamp devices 30 may each include the one or more light sources 62. At least one light source 62 may be configured to emit white light. Additionally or alternatively, at least one light source 62 may be configured to emit colored light (e.g., about 390 nm to about 700 nm). Further, at least one light source 62 may be configured to emit infrared light (e.g., about 700 nm to about 1 mm) and/or NIR light (e.g., about 700 nm to about 940 nm). Each of the one or more light sources 62 may be utilized in conjunction with and/or independently of other light sources 62 of the lamp device 30. The wearable medical device 10 may include the one or more light sources 62 that may or may not emit light 34 of the same wavelength. According to various aspects, the lamp devices 30 may include at least one filter. The filters may be colored filters that alter the color of the emitted light 34. The filters may also be polarized filters. It is contemplated that the filters may be integrated into the lamp device 30 or may be removable and/or interchangeable.

In various examples, the lamp devices 30 may be removable from the frame 14 or deactivated, such that the wearable medical device 10 may be used with or without the lamp devices 30. In such examples, the lamp devices 30 and the frame 14 may include magnets for magnetically coupling the lamp devices 30 to the frame 14. Alternatively, the lamp devices 30 may be clipped, snapped, fastened, or otherwise removably coupled to the frame 14. The lamp devices 30 may also be hot-swappable. Hot-swapping refers to the replacement or addition of components without stopping or deactivating the system as a whole. Accordingly, while the wearable medical device 10 is in use, the user 26 may remove, attach, and/or interchange the lamp devices 30 based on user preferences or the task being performed. This may provide flexibility in lighting for the surgical field 70, as well as the weight of the wearable medical device 10. Further, this may provide flexibility for using lamp devices 30 with different light sources 62 (e.g., configured to emit different wavelengths of light) and/or filters.

The light sources 62 of the lamp devices 30 and the light assembly 58 may include any form of light source 62. For example, fluorescent lighting, light-emitting diodes (LEDs), organic LEDs (OLEDs), polymer LEDs (PLEDs), laser diodes, quantum dot LEDs (OD-LEDs), solid-state lighting, a hybrid of these or any other similar device, and/or any other form of lighting may be utilized within the wearable medical device 10. Further, various types of LEDs are suitable for use as the light sources 62 including, but not limited to, top-emitting LEDs, side-emitting LEDs, and others. Moreover, according to various examples, multicolored light sources 62, such as Red, Green, and Blue (RGB) LEDs that employ red, green, and blue LED packaging may be used to generate various desired colors of light outputs from a single light source 62, according to known light color mixing techniques.

Figure 4:
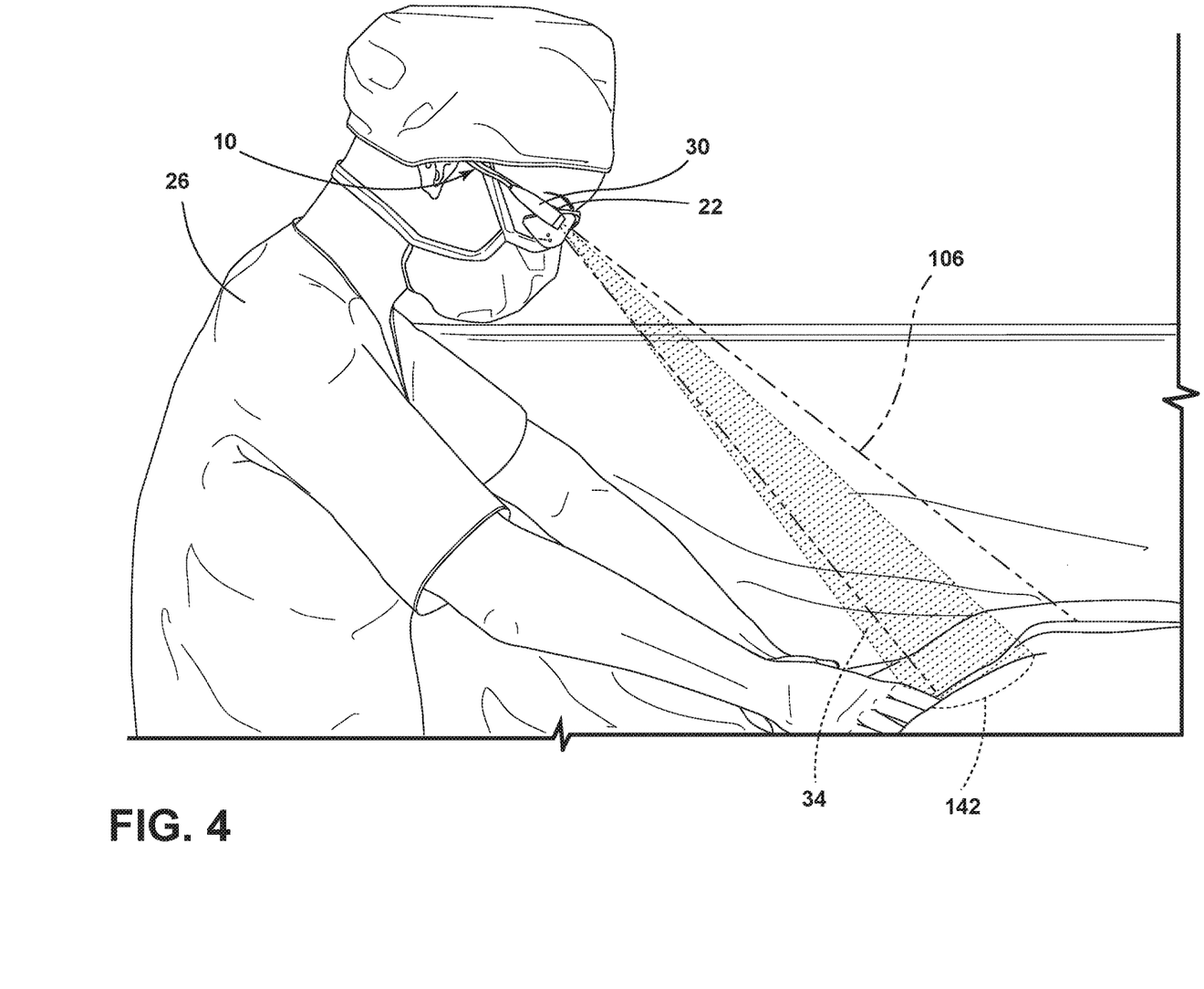
FIG. 4 is a schematic view of a wearable medical device having a light emission, according to one example.

With reference to FIG. 4, the lamp devices 30 are disposed substantially in line with the eyes 22 of the user 26 when the user 26 is wearing the wearable medical device 10. The positioning of the lamp devices 30 may provide for emissions of light 34 that substantially align with the field of vision 106 of the user 26. For example, the eye-ellipse of the user 26 may produce a field of vision 106 having an angle of about 10°. The lamp device 30 may include an emission of light 34 having an angle of about 20°. The emission of light 34 and the field of vision 106 may have a degree of overlap. In a specific example, the emission of light 34 and the field of vision 106 may have about a 5° degree overlap. However, it is contemplated that the emissions of light 34 and the field of vision 106 may have any degree of overlap without departing from the teachings herein.

Referring to FIG. 5, the controller 38 may be operably coupled with various components of the wearable medical device 10. The controller 38 may be integrated into the wearable medical device 10, or may be separate from the wearable medical device 10. In the illustrated configuration of FIG. 5, the controller 38 may include a processor 154, the memory 126, and other control circuitry. Commands or routines 158 are stored in the memory 126 and executable by the processor 154.

With reference to FIGS. 1 and 5, according to various aspects, the memory 126 includes an image analyzing routine. The controller 38 may correspond to one or more processors or circuits, which are configured to process image data received from the imager 96 and/or the image sensors 120. In this configuration, the image data may be communicated from the imager 96 and/or the image sensors 120 to the controller 38. The controller 38 may process the image data with one or more algorithms configured to determine an identity of the user 26 of the wearable medical device 10, the eye movement of the user 26, the fatigue metrics, and specific objects within the field of view 46. Further, the controller 38 may process the image data with one or more algorithms configured to determine the intensity and/or direction of the emitted light 34 within the surgical suite 54. The image analyzing routine may also be configured to identify shadows and luminosity within the surgical field 70. Additionally or alternatively, the memory 126 may include a light control routine for controlling the lamp devices 30 and the light assembly 58. The light control routine may auto adjust the intensity of one or more of the light sources 62 of the lamp devices 30 and/or the light assembly 58. Once the image analyzing routine has processed the data from the imager 96, the light control routine may control how the light assembly 58 and/or the lamp devices 30 are operated. For example, the light control routine may be configured to move, steer, activate, or otherwise influence the light assembly 58 and the lamp devices 30 to emit light 34 where the user 26 is looking or working (e.g., as detected from the imager 96 and image sensors 120). In such examples, the light assembly 58 may include one or more positioning devices 78 (e.g., a motor 82, actuator, etc.), for adjusting a position and/or projection direction of the light sources 62 within the light assembly 58. The lamp devices 30 may have the movable optics 138 to adjust the projection direction and the size of the light spot 142 of the light sources 62 of the lamp devices 30. The light control routine may selectively activate and/or steer the emitted light 34 from the light sources 62 adjusting an orientation, position, and/or a location of origin of the emissions of light 34 based on the shadows or variations in illumination of the surgical suite 54. In this way, the wearable medical device 10 may provide for the detection and selective illumination of various portions of the surgical suite 54.

In various examples, the image analyzing routine may also be configured to identify the location of a plurality of markers 114 within the image. The markers 114 may be symbols, computer readable codes, and/or patterns which designate a point of interest in the image. For example, the plurality of markers 114 can be positioned around the surgical field 70, such that the image analyzing routine may determine the perimeter of the surgical field 70. Further, one or more markers 114 may be positioned on the instruments 74, the user 26, points of interest in the surgical suite 54, and/or the patient.

In various aspects, the memory 126 may also include an eye tracking routine. In this way, the eye image data from the image sensors 120 is communicated to the controller 38, and the controller 38 determines the eye movement of the user 26. The controller 38 may then send a corresponding signal relating to the respective command associated with the eye movement. The memory 126 may further include a routine 158 relating to the fatigue metrics. Accordingly, a fatigue metrics routine may compare the detected eye image data from the image sensors 120 to baseline data. The memory 126 may also include an iris identification routine and may include saved settings and baseline data for the iris identification. In this way, the image sensors 120 and/or the IR sensors 122 may communicate the eye image data to the controller 38 and the controller 38 may identify the iris of the user 26. The controller 38 may then compare detected eye image data to saved image data in a database of information for selected user profiles.

Referring still to FIGS. 1 and 5, the wearable medical device 10 may be operably coupled to the light assembly 58 within the surgical suite 54. According to various aspects, the wearable medical device 10 may be coupled to the light assembly 58 via one or more wireless protocols (e.g., Bluetooth®; Wi-Fi (802.11a, b, g, n, etc.); ZigBee®; and Z-Wave®; etc.). The wearable medical device 10 may emit an indicator light 150 from the lamp devices 30 and/or a separate light source 62. The indicator light 150 may be visible or invisible to a human eye. In various aspects, the indicator light 150 may include white light, visible light, NIR emissions, and/or IR emissions. The indicator light 150 may be pulsed from the light source 62, or otherwise identified by the light assembly 58. Accordingly, the light assembly 58 includes a sensor 162 for sensing the indicator light 150. The indicator light 150 allows the light assembly 58 to sense where the wearable medical device 10 and, therefore, the user 26 are positioned. The wearable medical device 10 and the surgical suite 54 may include markers 114 configured to be sensed by the light assembly 58. In various examples, the table 66 and the instruments 74 may include the markers 114. The markers 114 may be visible to the human eye or may be IR markers 114. The markers 114 may allow the sensor 162 of the light assembly 58 to sense the presence of the user 26 in relation to other markers 114 within the surgical suite 54.

Additionally or alternatively, the light assembly 58 may include IR markers 114 and/or be configured to emit IR pulses or patterns. The imager 96 may be configured to detect the IR markers 114, pulses, and/or patterns from the light assembly 58. The information may be communicated to the controller 38, which may then determine the relative position of the light assembly 58 and the aim of the emitted light 34. This may be advantageous for repositioning the light assembly 58 and/or adjusting the intensity of the light 34 emitted from the light assembly 58.

The image sensors 120 may sense the eye movements that correspond to commands relating to the positioning of the light assembly 58. The commands may result in the light assembly 58 being repositioned and/or the intensity of the emitted light 34 being adjusted. The controller 38 may send a signal to the positioning devices 78 of the light assembly 58 and/or a light assembly control 166 for adjusting the position and/or angle of the light assembly 58. Further, the controller 38 may send a signal to the light assembly control 166 to adjust the intensity of the light 34 emitted from the light assembly 58. Control of the light assembly 58 via the wearable medical device 10 provides for increased efficiency for the user 26 in adjusting the light settings in the surgical suite 54. Accordingly, the light 34 settings may be adjusted without the user 26 stopping or pausing the medical treatment or procedure. Further, the wearable medical device 10 may provide for a more effectively lit cavity in the surgical field 70 with less light 34, which may also reduce pupil constriction of the user 26.

With further reference to FIGS. 1 and 5, the wearable medical device 10 provides for identifying contamination regions 170 that may require ultraviolet-C (UVC), or other, disinfection. The image sensors 120 may track the eye movement of the user 26, which may signify locations and/or a path that should be disinfected. In such aspects, the wearable medical device 10 may include a disinfecting mode. The controller 38 may include one or more algorithms relating to the disinfecting mode. In the disinfecting mode, the eye movements of the user 26 correlate to contaminated regions 170 that are in need of disinfecting, and may not correspond to any other user command. The contaminated regions 170 may correspond to regions where dirt, biological material, and/or bodily fluids (e.g., mucus, blood, saliva, urine, etc.) may be deposited in the surgical suite 54. Such material may be deposited as a result of one or more procedures or foreign contaminants shed by patients or personnel in the surgical suite 54.

According to one aspect of the present disclosure, a wearable medical device includes a frame and a lens coupled to the frame. The lens is configured to be positioned proximate to eyes of a user. At least one lamp device is coupled to the frame. The at least one lamp device emits light outward from the frame. A controller activates and controls the at least one lamp device.

According to another aspect, an image sensor is disposed on a lens and configured to capture eye image data.

According to still another aspect, an image sensor includes an iris authentication function.

According to yet another aspect, a controller controls at least one lamp device in response to eye image data captured by an image sensor.

According to another aspect, at least one lamp device includes a first lamp device and a second lamp device, and the first and second lamp devices are coupled to opposing side portions of a frame.

According to yet another aspect, at least one lamp device is disposed in a center portion of a frame.

According to still another aspect, an imager is disposed on a frame and configured to capture image data in a field of view.

According to another aspect of the present disclosure, a surgical suite illumination assembly includes a light assembly and a positioning device coupled to the light assembly. The light assembly is operable between a plurality of positions via the positioning device. A wearable medical device includes a frame, a lens coupled to the frame, and an image sensor coupled to the lens and configured to sense eye movement of a user. A controller controls at least one of the positioning device and the light assembly in response to the eye movement sensed by the image sensor.

Use of the present disclosure may provide for a variety of advantages. For example, the wearable medical device 10 may provide adjustable light settings within the surgical suite 54 and the cavity without the user 26 pausing their actions to make the adjustments manually. The wearable medical device 10 may also record images and sounds within the surgical suite 54, which may be reviewed later for teaching and other purposes. Additionally, the wearable medical device 10 may detect fatigue metrics of the user, which may be advantageous in a surgical setting. Additional benefits or advantages of using this device may also be realized and/or achieved.

It will be understood by one having ordinary skill in the art that construction of the described disclosure and other components is not limited to any specific material. Other exemplary embodiments of the disclosure disclosed herein may be formed from a wide variety of materials, unless described otherwise herein.

The present illustrated embodiments reside primarily in combinations of method steps and apparatus components related to a wearable medical device. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A wearable medical device, comprising:
a frame;
a support mechanism secured to the frame and configured to hold the frame in place on a user's head;
at least one sensor; and
an imager supported by the frame;
a controller in communication with the imager and with the at least one sensor;
at least one lamp device having a light source, the at least one lamp device removably securable to the frame and configured to be in communication with the controller;
wherein the at least one lamp device comprises movable optics capable of redirecting light from the light source in response to a received input;
wherein the imager is configured to:
capture and record images; and detect intensity of lighting in the environment surrounding the imager and to send a signal that corresponds to the lighting intensity to the controller.

2. The wearable medical device of claim 1, further comprising at least one lens coupled to the frame and configured to be positioned proximate eyes of a user when the wearable medical device is worn on a user's head.

3. The wearable medical device of claim 2, further comprising at least one image sensor disposed on the lens;
wherein the at least one image sensor is configured to capture eye image data of the user.

4. The wearable medical device of claim 3, wherein the at least one image sensor is configured to transmit inputs to the controller; and
wherein the controller is configured to, based on inputs received from the at least one image sensor, direct light emitted from the lamp device in a direction that substantially coincides with the direction of focus of the user.

5. The wearable medical device of claim 1,
wherein the imager has a lens; and
wherein the imager lens is polarized.

6. The wearable medical device of claim 1, wherein the controller is configured to process the captured images for stabilization data relating to one of the image and the lighting in the image.

7. The wearable medical device of claim 1, wherein the controller is configured to, upon receipt of the signal corresponding to the lighting intensity from the imager, adjust the intensity of light emitted from the lamp device in response to the signal.

8. The wearable medical device of claim 1, wherein the imager includes facial recognition functions;
wherein, upon capturing an image with a person's face, the imager is configured to send a signal to the controller; and
wherein, upon receipt of the signal, the controller is configured to deactivate the lamp device.

9. The wearable medical device of claim 1, wherein the imager is configured to detect display screens;
wherein, upon detecting a display screen, the imager is configured to send a signal to the controller; and
wherein, upon receipt of the signal from the imager, the controller is configured to deactivate the lamp device.

10. The wearable medical device of claim 1, wherein the controller is configured to:
process image data from images captured by the imager;
identify shadows and luminosity; and
adjust an intensity of the at least one lamp device based on the shadows and luminosity.

11. The wearable medical device of claim 1, further including a microphone disposed on the frame and configured to record sounds proximate the wearable medical device and to send audio information to one of the controller and an audio storage.

12. A surgical suite illumination system, comprising:
a light assembly, comprising
one or more light sources having adjustable intensity; and
one or more positioning devices operable to move the light assembly between a plurality of positions; and
a wearable medical device, comprising:
a frame;
a support member secured to the frame and configured to hold the frame in place on a user's head;
at least one sensor; and
a controller in communication with the at least one sensor and with the light assembly.

13. The surgical suite illumination system of claim 12, wherein the controller is configured to cause the light assembly to move based on inputs received from the at least one sensor.

14. The surgical suite illumination system of claim 12, wherein the controller is capable of causing the one or more light sources of the light assembly to change the intensity of the light they emit.

15. The surgical suite illumination system of claim 12, wherein the wearable medical device further comprises an infrared sensor in communication with the controller and configured to detect infrared patterns;
wherein the light assembly is configured to emit infrared patterns; and
wherein the controller is configured to use the detected infrared patterns from the wearable medical device to determine a relative position of the light assembly.

16. The surgical suite illumination system of claim 12, wherein the at least one sensor is configured to determine where a user is looking; and
wherein the controller is configured to position the light assembly to provide light where the user is looking.

17. The surgical suite illumination system of claim 12, further comprising an imager in communication with the controller and configured to capture image data;
wherein the controller is configured to:
process image data from images captured by the imager;
identify shadows and luminosity; and
cause the one or more positioning devices to move the light assembly based on the shadows and luminosity.

* * * * *